United States Patent
Kang et al.

(10) Patent No.: US 9,862,978 B2
(45) Date of Patent: Jan. 9, 2018

(54) METHOD FOR PREPARING (2RS)-AMINO-(3S)-HYDROXY-BUTYRIC ACID AND ITS DERIVATIVES

(71) Applicant: AMINOLOGICS Co., Ltd., Seoul (KR)

(72) Inventors: Min Seok Kang, Yongin-si (KR); Hyun Il Lee, Seongnam-si (KR); Ki Nam Uhm, Daejeon (KR); Jin Hyang Kim, Cheonan-si (KR)

(73) Assignee: Aminologics Co. Ltd., Gangnam-Gu, Seoul (KR)

( * ) Notice: Subject to any disclaimer, the term of this patent is extended or adjusted under 35 U.S.C. 154(b) by 0 days.

(21) Appl. No.: 14/770,445

(22) PCT Filed: Feb. 24, 2014

(86) PCT No.: PCT/KR2014/001478
§ 371 (c)(1),
(2) Date: Aug. 25, 2015

(87) PCT Pub. No.: WO2014/133291
PCT Pub. Date: Sep. 4, 2014

(65) Prior Publication Data
US 2016/0017389 A1  Jan. 21, 2016

(30) Foreign Application Priority Data

Feb. 26, 2013  (KR) .................. 10-2013-0020365

(51) Int. Cl.
C12P 13/04 (2006.01)
C07C 227/20 (2006.01)
C07C 229/22 (2006.01)

(52) U.S. Cl.
CPC ............ C12P 13/04 (2013.01); C07C 227/20 (2013.01); C07C 229/22 (2013.01)

(58) Field of Classification Search
CPC ....... C12P 13/04; C07C 229/22; C07C 227/20
See application file for complete search history.

(56) References Cited

U.S. PATENT DOCUMENTS

| 4,211,840 A | 7/1980 | Nakamori et al. |
| 8,835,436 B2 | 9/2014 | Lee et al. |

FOREIGN PATENT DOCUMENTS

| EP | 1416050 A1 | 5/2004 |
| KR | 20030036199 A | 5/2003 |
| KR | 1020040014655 A | 2/2004 |
| WO | 0140450 A1 | 6/2001 |
| WO | 2011005052 A2 | 1/2011 |

OTHER PUBLICATIONS

Seo et al. J. Med. Chem. (2011) 54 (18), 6305.*
Keto et al. Biosci. Biotechnol. Biochem. (1993) 57 (2) 303-307 (abstract only).*
Kato et al. Purification and Properties of Aldehyde Reductases from Yeasts That Convert Ethyl 2-Acetamido-3-oxobutyrate to Optically Active Ethyl 2-Acetamido-3-hydroxybutyrate., Bioscience, biotechnology, and biochemistry (1993), vol. 57(2), pp. 303-307.*
International Search Report dated Jun. 2, 2014 and its English language translation from corresponding International Application No. PCT/KR2014/001478.
Online posting about (2S,3R)2-acetamido-3-hydroxybutanoate. [online]Pubchem. Jul. 29, 2006, Internet:<http://pubchem.ncbi.nlm.nih.gov/search/#collection=compounds> See structural formula.

* cited by examiner

*Primary Examiner* — Alexander D Kim
(74) *Attorney, Agent, or Firm* — Arent Fox LLP

(57) ABSTRACT

The present invention relates to a method for easily preparing (2RS)-amino-(3S)-hydroxy-butyric acid, which is a chiral amino acid, in a high yield and a high purity using a chemical synthesis and enzymatic reduction reaction; an intermediate therefor; and a method for preparing the intermediate.

3 Claims, No Drawings

METHOD FOR PREPARING (2RS)-AMINO-(3S)-HYDROXY-BUTYRIC ACID AND ITS DERIVATIVES

TECHNICAL FIELD

The present invention relates to a preparation of (2RS)-amino-(3S)-hydroxy-butyric acid or its derivatives and to the intermediates for preparing the same. Specifically, the present invention relates to a preparation of (2RS)-amino-(3S)-hydroxy-butyric acid or its derivatives by using a chemical synthesis and an enzymatic synthesis from a mixture of unnatural amino acids of D-(2R,3S)-threonine and L-allo-(2S,3S)-threonine to obtain (2RS)-amino-(3S)-hydroxy-butyric acid in a high yield and in a high purity and to the intermediates for preparing the same.

BACKGROUND ART

L-threonine, which is one of natural amino acids, is widely employed as feeding materials and food additives as well as a raw material for the synthesis or production of rehydration solution or other medicines. D-threonine and D- or L-allo-threonine are unnatural amino acids and can also be considered as useful chiral building blocks.

Threonine having a general name of 2-amino-3-hydroxy-butyric acid has two chiral centers at 2-position and 3-position in its molecule and thus has 4 stereoisomers including, specifically, L-(2S,3R)-threonine (Formula 1), D-(2R,3S)-threonine (Formula 2), D-allo-(2R,3R)-threonine (Formula 3) and L-allo-(2S,3S)-threonine (Formula 4) as follows:

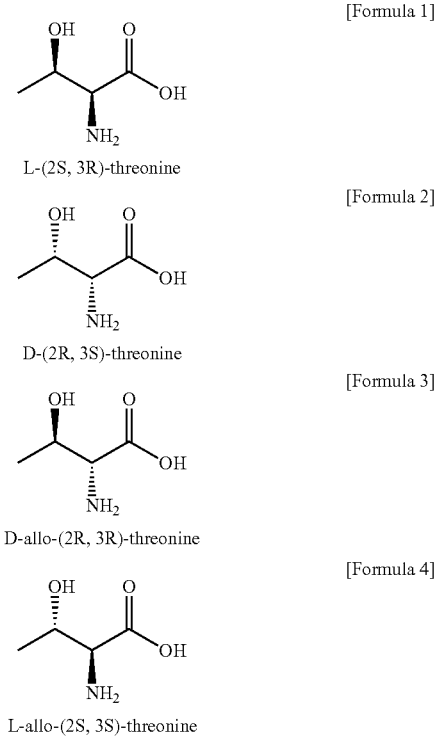

A reference article [Organic Syntheses, Coll. Vol. 3, p. 813 (1955); Vol. 20, p. 101 (1940)] discloses a preparation of D, L-threonine in a racemic form containing all 4 isomers through all 8 steps from crotonic acid as the starting material.

Korean Patent Laid-Open Publication No. 2003-0036199 discloses an enzymatic preparation of natural amino acid of L-threonine using *Enterobacters*. In addition, methods of preparing L-threonine by an enzymatic method via gene recombination are disclosed in several patents and references.

A reference article [Tetrahedron: Asymmetry Vol. 2, No. 1, pp. 555-561. 1991] discloses a stereoselective preparation of D-threonine and L-threonine using a ruthenium catalyst.

U.S. Pat. No. 4,211,840 discloses a preparation of D-threonine by using a microorganism or an enzyme, which comprises cultivating a microorganism that uses a hydantoin derivative as a nitrogen source and contacting the cultivated microorganism with various hydantoin derivatives to prepare several type of D-amino acid including D-threonine. However, there is a problem that the yields in most of Examples of said patent do not exceed 50%.

WO 01/40450A1 discloses a preparation of chiral alcohol compounds which are a raw material of a hyperlipidemia treating drug by reducing a ketone compound using a reductive enzyme.

A know reference [Helv. Chim. Acta vol 70; 232-236, 1987] disclosed a preparation of L-threonine by reducing a ketone using a microorganism, but there may be problems that the commercial viability is low since the yield is very low, for example about 16%, and that side products that are difficult to be separated are simultaneously generated.

As such, there has been necessity for a method of preparing economically and in a high yield D-threonine and L-allo-threonine which are expensive amino acids and importantly employed in new drug development and chemical synthesis.

Meanwhile, research has been largely performed on the preparation of expensive amino acids by an enzymatic reduction using a microbial reductive enzyme to prepare expensive amino acids which can be importantly employed in new drug development and chemical synthesis. However, although there have been many researches on the preparation of chiral alcohol by an enzymatic reduction, there is little research on the preparation of chiral amino acids.

In enzymatic reduction methods, genes corresponding to reductive enzyme are separated from microbials which are novel microbials isolated from natural world or which are known in articles or patents, said genes are transferred into a plasmid and then transformed in *E. coli*, which is cultivated. Said cultivated *E. coli* is separated and employed in an enzymatic reaction. In another way, said cultivated *E. coli* is broken and centrifuged to obtain a supernatant, which is used in the enzymatic reaction.

PRIOR ART

Patent Documents

1. Korean Patent Laid-Open No. 2003-0036199
2. U.S. Pat. No. 4,211,840
3. WO01/40450A1

Non-Patent Documents

1. Organic Syntheses, Coll. Vol. 3, p. 813 (1955)
2. Organic Syntheses, Coll. Vol. 20, p. 101 (1940)
3. Tetrahedron: Asymmetry Vol. 2, No. 1, pp. 555-561. 1991
4. Helv. Chim. Acta vol 70; 232-236, 1987

SUMMARY

In one aspect of the invention there has been found a method for the preparation of (2RS)-amino-(3S)-hydroxybutyric acid or its derivative of Formula 5, comprising obtaining the compound of Formula 9 from the compound of Formula 8 by an enzymatic reduction:

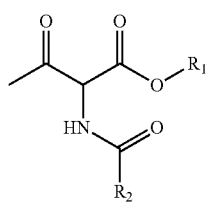

[Formula 5]

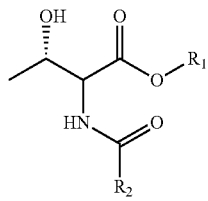

[Formula 8]

[Formula 9]

wherein, $R_1$ represents hydrogen, a linear or branched $C_1$~$C_4$ alkyl group, an alkylcarbonyl group, an alkoxycarbonyl group, a phenyl group, a benzyl group or a phenethyl group and wherein said alkyl can be unsubstituted or substituted with hydroxy or halogen, wherein $R_2$ represents a linear or branched $C_1$~$C_4$ alkyl group, an alkylcarbonyl group, an alkoxycarbonyl group, a phenyl group, a benzyl group or a phenethyl group, wherein said alkyl can be unsubstituted or substituted with hydroxy or halogen and wherein $R_1$ can be the same or different than $R_2$.

And in one aspect of the inventive method the preparation comprises the steps (i), (ii), (iii) and (iv):

(i) a step of the reaction of 3-oxo-butyric acid alkyl ester of Formula 6 with sodium nitrite to obtain 2-hydroxyimino-3-oxo-butyric acid alkyl ester of Formula 7;

(ii) a step of the reduction or hydrogenation of the compound of Formula 7 to obtain (2RS)-alkylcarbonylamino-3-oxo-butyric acid alkyl ester of Formula 8;

(iii) a step of the enzymatic reduction of the compound of Formula 8 to obtain (2RS)-alkylcarbonylamino-(3S)-hydroxy-butyric acid alkyl ester of Formula 9;

(iv) a step of the deprotection of the compound of Formula 9 to prepare (2RS)-amino-(3S)-hydroxy-butyric acid of Formula 5.

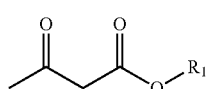

[Formula 6]

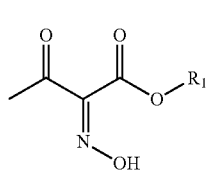

[Formula 7]

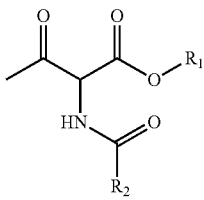

[Formula 8]

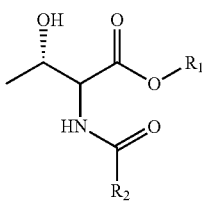

[Formula 9]

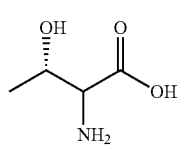

[Formula 5]

wherein, $R_1$ represents hydrogen, a linear or branched $C_1$~$C_4$ alkyl group, an alkylcarbonyl group, an alkoxycarbonyl group, a phenyl group, a benzyl group or a phenethyl group and wherein said alkyl can be unsubstituted or substituted with hydroxy or halogen, wherein $R_2$ represents a linear or branched $C_1$~$C_4$ alkyl group, an alkylcarbonyl group, an alkoxycarbonyl group, a phenyl group, a benzyl group or a phenethyl group, wherein said alkyl can be unsubstituted or substituted with hydroxy or halogen and wherein $R_1$ can be the same or different than $R_2$.

In one aspect of the inventive method the enzymatic reduction is carried out by employing a reductive enzyme or a fraction containing the reductive enzyme, said reductive enzyme being issued from one or more microbials selected from a group consisting of *Saccharomyces, Lactobacillus, Candida, Rhodococcus, Pseudomonas* or *Pichia*. In a further aspect, the enzymatic reduction is carried out by employing a reductive enzyme or a fraction containing the reductive enzyme, said reductive enzyme being issued from one or more microbials selected from a group consisting of *Candida magnolia, Candida parapsilosis, Rhodococcus erythropolis* and *Devosia riboflavina*. And in a still further aspect, the enzymatic reduction is carried out by employing a reductive enzyme or a fraction containing the reductive enzyme, said reductive enzyme being issued from one or more microbials selected from a group consisting of *Candida magnolia*-possessing reduction enzyme, *Candida parapsilosis*-possessing reduction enzyme, *Rhodococcus erythropolis*-possessing reduction enzyme and *Devosia riboflavina*-possessing reduction enzyme.

In one aspect of the inventive method, the hydrogenation of the step (ii) is carried out by using one or more reagent selected from a group consisting of acetic anhydride, di-tert-butyl-dicarbonate or benzyl chloroformate in the presence of palladium/carbon with hydrogen gas. And in one aspect, the deprotection of the step (iv) is carried out by using hydrochloric acid in an alcoholic solvent such as ethanol.

In another aspect of the invention there has been discovered a composition of matter comprising (2RS)-alkylcarbonylamino-(3S)-oxo-butyric acid alkyl ester or its derivatives represented by Formula 8:

[Formula 8]

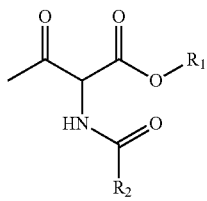

In still another aspect of the invention there has been discovered a composition of matter comprising (2RS)-alkylcarbonylamino-(3S)-hydroxy-butyric acid alkyl ester or its derivatives represented by Formula 9:

[Formula 9]

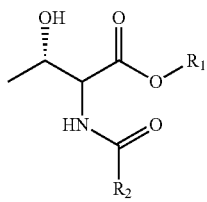

DETAILED DESCRIPTION

Technical Subject

One aspect of the present invention is to provide a commercially advantageous method of efficiently preparing and easily separating an isomer of threonine or its mixture among 4 isomers of threonine, wherein said isomer of threonine is not available in the nature or a mixture containing the isomer.

Means for Achieving the Subject

The inventors of the present invention have studied in order to develop a method of efficiently preparing (2RS)-amino-(3S)-hydroxy-butyric acid and its derivatives in which the alcohol group at 3-position of the threonine has a S-configuration, and as a result, have finally developed an efficient method of preparing, in a high yield and in a high purity, D-threonine and L-allo-threonine in which the alcohol group at 3-position of the threonine has a S-configuration by using a chemical reaction and an enzymatic reductive reaction.

In other words, the inventors of the present invention have achieved to prepare a mixture of D-threonine (2R,3S) of Formula 2 and L-allo-threonine (2S,3S) of Formula 3, that is, to prepare (2RS)-amino-(3S)-hydroxy-butyric acid of Formula 5 or its derivatives in a high yield and in a high purity.

[Formula 5]

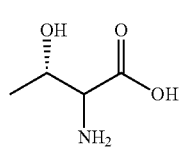

Effect of Invention

According to one aspect the present invention, (2RS)-amino-(3S)-hydroxy-butyric acid or its derivatives which is a mixture of partial isomer of threonine can be prepared in a high yield and in a high purity.

EMBODIMENTS FOR CARRYING OUT THE INVENTION

One aspect of the present invention is to provide a method of preparing (2RS)-amino-(3S)-hydroxy-butyric acid of Formula 5 or its derivatives, comprising a step of obtaining (2RS)-alkylcarbonylamino-(3S)-hydroxy-butyric acid alkyl ester or its derivatives from by (2RS)-alkaneamido-3-oxo-butyric acid alkyl ester or its derivatives by the enzymatic reduction method.

[Formula 5]

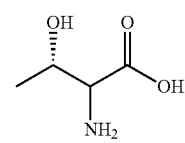

Said method can be provided by obtaining a threonine in which its 3-position (beta position) holds S-configuration and its 2-position (alpha position) is a mixture of R-form and S-form by an enzymatic reduction method, as illustrated in below Reaction Formula 1.

[Reaction Formula 1]

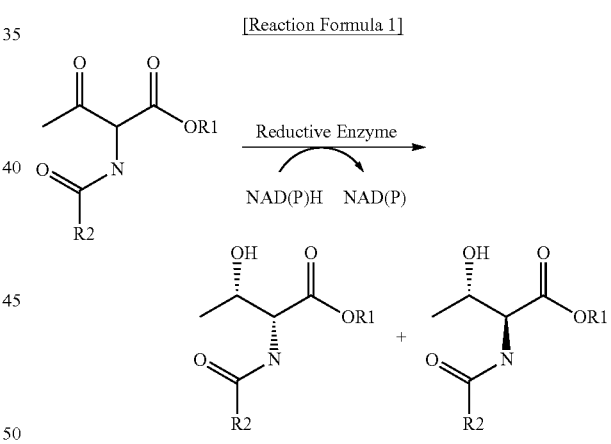

In the Reaction Formula 1, R1 represents hydrogen, linear or branched alkyl, preferably $C_1$~$C_4$ alkyl, alkylcarbonyl, alkoxycarbonyl, phenyl, benzyl or phenethyl, and $R_2$ represents linear or branched alkyl, preferably $C_1$~$C_4$ alkyl, phenyl, benzyl or phenethyl, said alkyl is preferably $C_1$~$C_4$ alkyl unsubstituted or substituted with hydroxy or halogen.

According to one aspect of the present invention, the method of preparing (2RS)-amino-(3S)-hydroxy-butyric acid or its derivatives can involve the below steps (i), (ii), (iii) and (iv):

(i) a step of reacting 3-oxo-butyric acid alkyl ester of Formula 6 with sodium nitrite to obtain 2-hydroxyimino-3-oxo-butyric acid alkyl ester of Formula 7;

(ii) a step of reducing or hydrogenating the compound of Formula 7 to obtain (2RS)-alkylcarbonylamino-3-oxo-butyric acid alkyl ester of Formula 8;

(iii) a step of subjecting the compound of Formula 8 to the enzymatic reduction to obtain (2RS)-alkylcarbonylamino-(3S)-hydroxy-butyric acid alkyl ester of Formula 9;

(iv) a step of deprotecting the compound of Formula 9 to prepare (2RS)-amino-(3S)-hydroxy-butyric acid of Formula 5.

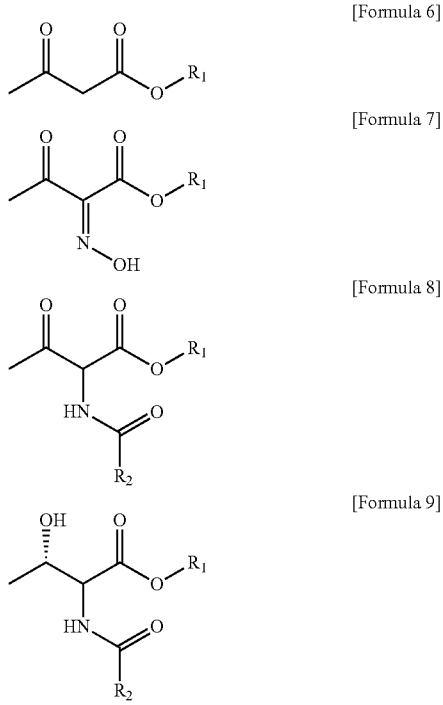

(in the above formulae, $R_1$ and $R_2$ are the same as defined in the above.)

Another aspect of the present invention is to provide the compound of Formula 7 and the compound of Formula 8 as intermediates which can be employed in the preparation of (2RS)-amino-(3S)-hydroxy-butyric acid or its derivatives.

And still another aspect of the present invention is to provide the preparation of the compound of Formula 7 and the compound of Formula 8.

In one aspect the present invention, the compound of Formula 7 can be obtained by a method comprising the above step (i), and the compound of Formula 8 can be obtained by a method comprising the above step (ii).

According to one aspect the present invention, the hydrogenation of the step (iii) can be carried out with hydrogen gas under palladium/carbon catalyst, and it is possible to employ reagents such as organic acid anhydride such as acetic anhydride, di-tert-butyl dicarbonate, or chloroformate such as benzyl chloroformate.

The enzymatic reduction of the step (iv) can be carried out by using a reductive enzyme or a fraction containing the same, wherein said reductive enzymes are issued from one or more microorganisms selected from a group consisting of *Saccharomyces, Lactobacillus, Candida, Rhodococcus, Pseudomonas* or *Pichia*.

And in a further aspect, said enzymatic reduction can be carried out by using a reductive enzyme or a fraction containing the same, wherein said reductive enzymes are issued from one or more microorganisms selected from a group consisting of *Candida magnolia, Candida parapsilosis, Rhodococcus erythropolis* and *Devosia riboflavina*. In a still further aspect, said enzymatic reduction can be carried out by using a reductive enzyme selected from a group consisting of *Candida magnolia*-possessing reduction enzyme, *Candida parapsilosis*-possessing reduction enzyme, *Rhodococcus erythropolis*-possessing reduction enzyme and *Devosia riboflavina*-possessing reduction enzyme.

In one aspect of the present invention, a microbial reductive enzyme or a microbial-possessing reductive enzyme means the enzyme wherein the reductive enzyme contained in the microbial possesses is microbially cultivated, separated and/or purified and/or the enzyme wherein the reductive enzyme contained in the microbial possesses is genetically transformed, cultivated, separated and/or purified. It is possible to employ a commercially available enzyme.

And in one aspect of the present invention, the deprotection of the step (v) can be carried out by using any method and reagents which can be used in a deprotection of an ester protecting group or an alkanamido protecting group, for example, can be carried out by using an acid catalyst such as hydrochloric acid in an alcoholic solvent such as ethanol.

In below, by referring to Reaction Formula 2, the preparation of (2RS)-amino-(3S)-hydroxy-butyric acid or its derivatives will be more specifically described. The method illustrated in Reaction Formula 2 is only a typical example among methods used in the present invention and the, reaction reagents, reaction condition or the like may be optionally varied.

[Reaction Formula 2]

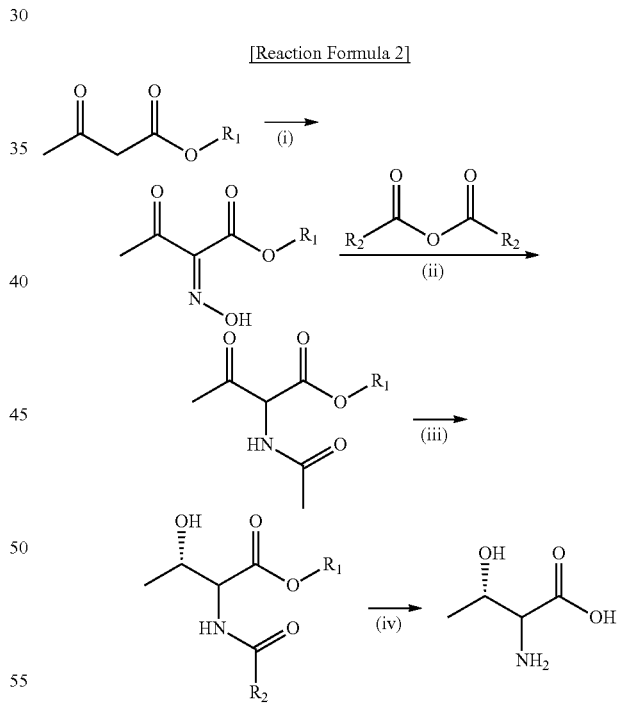

The above step (i) is a reaction of attaching a hydroxyimino group wherein 3-oxo-butyric acid alkyl ester of Formula 6 is reacted with sodium nitrite ($NaNO_2$) to obtain an oxime compound of Formula 7. The reaction temperature may be selected from −20~0° C. and the reaction solvent may be acetic acid, water or a mixture thereof. It is preferable to employ sodium nitrite in an amount of 1~2 equivalent.

The step (ii) in the Reaction Formula 2 is a catalytic reduction or hydrogenation of the hydroxyimino group, wherein 2-(hydroxyimino)-3-oxo-butyric acid alkyl ester of Formula 7 is subjected to a reduction or hydrogenation to obtain (2RS)-alkylcarbonylamino-3-oxo-butyric acid alkyl ester of Formula 8. The step (ii) can be carried out by using 0.2~0.5 equiv. of 10% palladium/carbon and 2~3 equiv. of organic acid anhydride (e.g. acetic anhydride) or di-tert-butyl-dicarbonate in an alcohol solvent such as ethanol under hydrogen gas of 1~5 atm, or can be achieved by a hydrogenation in the presence of chloroformate compound (e.g. benzyl chloroformate).

The step (iii) of in the Reaction Formula 2 is a enzymatic reduction reaction, wherein (2RS)-alkylcarbonylamino-3-oxo-butyric acid alkyl ester of Formula 8 is subjected to an enzymatically or microbially asymmetric reduction to obtain (2RS)-alkanamido-(3S)-hydroxybutyric acid ester of Formula 9. The enzymatic reduction is generally carried out in water, the reaction temperature can be selected from generally 10~40° C., particularly around room temperature, and pH of the reaction solution may be maintained about 6.5.

The reduction enzymes which can be employed can be issued from one or more microorganisms selected from microorganisms belonged to *Saccharomyces, Lactobacillus, Candida, Rhodococcus, Pseudomonas* or *Pichia*, and specifically can be selected from a group consisting of such as *Candida magnolia*-possessing reduction enzyme, *Candida parapsilosis*-possessing reduction enzyme, *Rhodococcus erythropolis*-possessing reduction enzyme and *Devosia riboflavina*-possessing reduction enzyme.

The step (iv) is a deprotection reaction wherein (2RS)-alkylcarbonylamino-(3S)-hydroxybutyric acid alkyl ester of Formula 9 is deprotected to obtain (2RS)-amino-(3S)-hydroxy-butyric acid of Formula 5. The step (iv) is carried out, for example, by adding 3N hydrochloric acid into the reactant and refluxing for 3 hours to simultaneously remove acetyl, tert-butoxycarbonyl (Boc) or benzyloxycarbonyl (Cbz) attached to the amine group together with ester group attached to carboxylic acid group. As reaction solvent, water, ethanol, methanol, isopropanol, ethyl acetate, or the like can be employed, and ethanol is particularly preferred. The deprotection reaction of acetoamido, tert-butoxycarbonyl (Boc) or benzyloxycarbonyl (Cbz) and/or ester group is not specifically restricted and any one of both may be selectively deprotected.

In an aspect of the present invention, derivatives of (2RS)-amino-(3S)-hydroxy-butyric acid Formula 5 and derivatives of other compounds mean compounds wherein their reactive group such as amino group, hydroxy group and/or carboxylic acid group contained in the compounds are substituted or protected with a substituent or protecting group. The type of protecting group of said amino group, hydroxy group and/or carboxylic acid group is not particularly limited, and a protecting group which is generally used in the field can be employed. For example, amino group can be protected in the form of mono- or dialkylamino, alkylamino, alkylimido, alkylcarbonylamino, alkoxycarbonylamino or the like, hydroxy group can be protected in the form of alkylether, alkylcarbonyloxy or the like, and carboxylic acid group can be protected in the form of alkylester, alkylamide or the like.

In an aspect of the present invention, the enzymatic reduction or enzymatic reductive reaction is a reaction for forming a hydroxyl group by reducing ketone or aldehyde group of an organic compound by using a microbial itself or a reductive enzyme issued from a microbial. The reduction enzyme or reductive enzymes issued from a microbial means a reductive enzyme which is extracted from natural-occurring microbials or genetically modified microbials or a mixture or fraction containing the reductive enzyme. The reductive enzyme which can be employed in the enzymatic reduction can include oxidation-reduction enzymes (EC 1.1, alcohol oxidoreductases) which act as a donator for CH—OH group or oxidation-reduction enzymes (EC 1.2) which act as a donator for oxo group, but is not restricted thereto.

The reductive enzymes issued from the microbials or the fraction containing the reductive enzymes can be prepared by a method described in, for example, a reference [Maniatis, T. (1989) Molecular cloning: a laboratory manual, 2nd ed., Cold Spring Harbor Laboratory Press, New York] by a person having ordinary skill in the art. Specifically, a gene corresponding to reductive enzyme is duplicated from an objective microbial by using PCT method, cut at its specific positions by using a restriction enzyme, linked at a specific site of a plasmid by using ligase to prepare a recombined DNA-plasmid. Thus obtained recombined DNA-plasmid is transformed in *E. coli*, cultivated and centrifuged to recover the cultivated microbials, which is then broken by an ultra-sonication, centrifuged, and separated from the solid portion to obtain a fraction containing reductive enzymes.

The types of microorganisms from which the reduction enzymes that can be employed would be issued is not specifically restricted, but in particular, can include microorganisms belonged to, for example, *Saccharomyces, Lactobacillus, Candida, Rhodococcus, Pseudomonas* or *Pichia*.

Meanwhile, the reduction enzymes which can be preferably employed in one aspect of the present invention such as *Candida magnolia*-possessing reduction enzyme, *Candida parapsilosis*-possessing reduction enzyme, *Rhodococcus erythropolis*-possessing reduction enzyme and *Devosia riboflavina*-possessing reduction enzyme can be easily prepared by a known method described in a literature [Maniatis, T. (1989) Molecular cloning: a laboratory manual, 2nd ed., Cold Spring Harbor Laboratory Press, New York], but is not limited to them which are prepared by a method described in said literature.

The present invention has advantages that the starting material is easily available and that it is possible to prepare (2RS)-amino-(3S)-hydroxy-butyric acid (Formula 5) having a high price in a high yield and a high purity from starting materials.

In below, aspects of the present invention are specifically explained by Examples. These Examples is provided only for the explanation of the present invention and it is obvious to a person having ordinary skill in the art that the present invention is not restricted only to the Examples.

Example 1: Preparation of ethyl 2-(hydroxyimino)-3-oxobutanoate

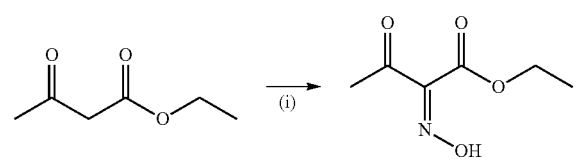

In a reactor ethyl acetoacetate 30.0 g and acetic acid 35 ml are introduced and stirred at −10° C. to obtain a stirred solution, to which a solution of sodium nitrite 18.0 g in a purified water 40 ml is slowly and dropwise added while maintaining the temperature of the stirred solution at −10° C., and then a cold ice water 120 ml is additionally dropwise added. After the completion of the dropwise addition, the resulting reaction mixture is warmed to the room temperature and further stirred for 3 hours at the room temperature. After confirming the total consumption of starting materials by TLC (developing solution=heptane:ethyl acetate=2:1), the reaction mixture is extracted 3 times with 300 ml of a 4:1 solution of ethyl acetate:tetrahydrofuran. The extracted organic layer is washed twice with 50 ml of a saturated solution of sodium bicarbonate, dried under anhydrous magnesium sulfate, filtered and concentrated under a reduced pressure. Thus obtained concentrate is dried under vacuum to give a titled compound of 2-(hydroxyimino)-3-oxobutanoate 33.7 g (yield 92%).

$^1$H-NMR (400 MHz, DMSO-d6): δ 13.20 (s, 1H), 4.21 (q, J=7.2 Hz, 2H), 2.32 (s, 3H), 1.92 (t, J=6.8 Hz, 3H).

Example 2: Preparation of ethyl (2RS)-acetoamido-3-oxobutanoate

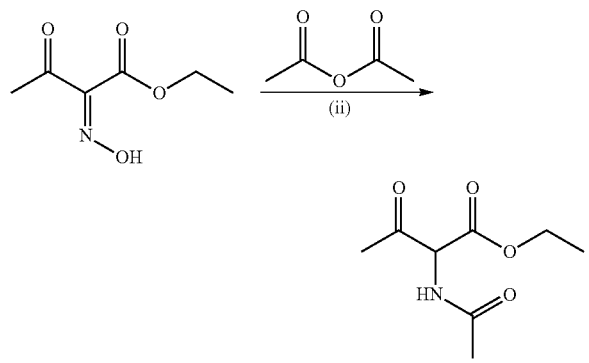

In a autoclave reactor, ethyl 2-(hydroxyimino)-3-oxobutanoate 10.0 g obtained in Example 1, ethanol 40 ml, acetic anhydride 11 ml and 10% palladium/carbon 0.1 g are introduced, hydrogen gas is introduced to adjust the pressure to 42 psi, and stirred for 12 hours at the normal temperature. After the completion of the reaction, palladium/carbon is filtered off and the filtrate is concentrated. The resulting concentrate is purified by a silica gel column chromatography (ethyl acetate:heptane=1:1) to give the titled compound of ethyl 2-acetoamido-3-oxobutanoate 10.5 g (yield 90%).

$^1$H-NMR (400 MHz, CDCl$_3$): δ 6.62 (br s, 1H), 5.25 (d, J=6.4 Hz, 1H), 4.28 (q, J=7.2 Hz, 2H), 2.39 (s, 3H), 2.07 (s, 3H), 1.32 (t, J=7.2 Hz, 3H).

Example 3: Preparation of (2RS)-tert-butoxycarbonylamino-3-oxo-butyric acid ethyl ester

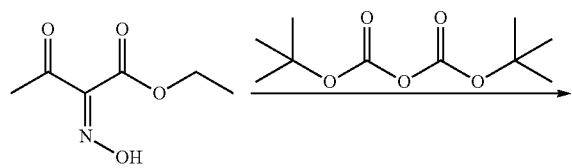

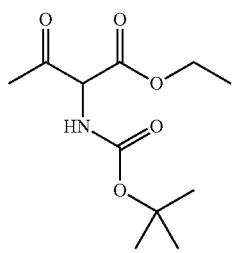

In a autoclave reactor, ethyl 2-(hydroxyimino)-3-oxobutanoate 16.0 g obtained in Example 1, ethanol 40 ml, di-tert-butyl dicarbonate 23.0 g and 10% palladium/carbon 0.4 g are introduced, hydrogen gas is introduced to adjust the pressure to 100 psi, and stirred for 12 hours at the normal temperature. After the completion of the reaction, palladium/carbon is filtered off and the filtrate is concentrated. The resulting concentrate is purified by a silica gel column chromatography (ethyl acetate:heptane=1:2) to give the titled compound of ethyl 2-tert-butoxycarbonylamino-3-oxo-butyric acid ethyl ester 14.0 g (yield 61%).

$^1$H-NMR (400 MHz, CDCl$_3$): δ 5.75 (br s, 1H), 5.03 (d, J=6.8 Hz, 1H), 4.26 (m, 2H), 2.36 (s, 3H), 1.44 (s, 3H), 1.21 (t, J=7.2 Hz, 3H).

Preparation Example 1: Separation and Extraction of Reduction Enzymes Possessed in Microorganisms The enzymes listed in Table 1 are prepared according to the method described in a literature [Appl Microbiol Biotechnol. vol 64, p. 359 (2004)].

After each microbial is cultivated in a cultural medium, the chromosome is extracted and purified, and then the reduction enzyme is amplified by employing a designed PCR primer. The band having a desired size is confirmed at the electrophoresis, extracted and purified, cut by using a restriction enzyme, and mixed with an expression vector which has been cut and purified with the same restriction enzyme, and then linked with a ligase. Thus prepared recombined DNA is transformed at E. coli, a bacterial community having the activity is selected and cultivated in a medium. The bacterial community is recovered by a centrifugation, broken by the ultrasonication, and centrifuged to prepare a supernatant possessing reduction enzymes.

Test Example 1: Test of Screening Enzymes for the Preparation of ethyl (2RS)-acetoamido-(3S)-hydroxybutanoate

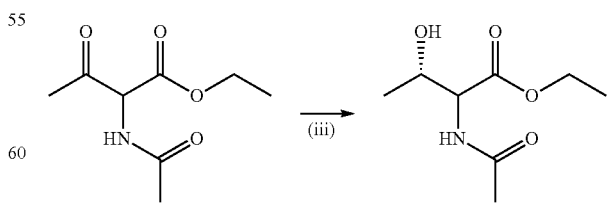

By employing, as an enzyme, reductive enzymes listed in Table 1 and, as a substrate, ethyl 2-acetoamido-3-oxobutanoate prepared in Example 2, a test of screening enzymes is carried out as described in below.

In a general screen test of enzymes, there may be a much difference in the specificity against to the substrate and/or reaction of the enzyme according to the type of enzyme. Therefore, it is necessary to perform many experiments on various microbials in order to seek optimal enzymes matching well to the desired object. In the screen test of enzymes, tests on various microbials have been carried out in order to screen excellent reductive enzymes since there would be a difference in the stereospecificity of the reductive enzymes depending on the type of microbials.

To a 50 mM phosphoric acid solution (pH=7) 0.6 ml, NAD 2 mM, NADP 2 mM, glucose 2%, the substrate 6 mg and reduction enzyme 1 mg are added and reacted under stirring for 16 hours. Samples are taken from the resulted reaction product to be analyzed by a gas chromatography mounted with a chiral column [Chirasil-DEX CB 25 m×0.25 mm, produced by Chrompak Company]. The results are described at Table 1 (The results of screen of reduction enzymes in microorganisms).

TABLE 1

| Microbials | allo-Threonine (L/D) L-allo-(2S,3S)/ D-allo-(2R,3R) | Threonine (L/D) L-(2S,3R)/ D-(2R,3S) |
|---|---|---|
| Saccharomyces cerevisiae | 6.5%/16.9% | 1.7%/10.9% |
| Candida magnoliae | 38.3%/0 | 0/23.8% |
| Lactobacillus buchneri | 2.8%/0 | 0/3.5% |
| Lactobacillus brevis | 3%/0 | 0/42.8% |
| Candida parapsilosis | 43%/0 | 0/17% |
| Streptococcus faecium | 23.5%/0 | 0/5.2% |
| Streptococcus lividans | 0/0 | 0/0 |
| Gluconobacter oxydans | 7.7%/0 | 0/11% |
| Corynebacterium sp. | 5.2%/23% | 11.4%/6.6% |
| Pseudomonas putida | 2.3%/0 | 0/3% |
| Pseudomonas aeruginosa | 1.3%/1.2% | 0/2% |
| Proteus vulgaris | 2.5%/0 | 3%/0 |
| Alcaligenes eutrophus | 1%/0.6% | 0/1.7% |
| Nocardia sp. | 2.7%/0 | 0/4.1% |
| Rhodococcus erythropolis | 22%/0 | 0/77.8% |
| Rhodococcus rhodochrous | 8.9%/0 | 0/18.4% |
| Pichia pastoris | 3.3%/0 | 0/5.2% |
| Pichia angusta | 12.8%/0 | 0/17.1% |
| Rhodococcus rubber | 17%/0 | 0/3.2% |
| Pichia methanolica | 5.9%/1.2% | 0/7.6% |
| Devosia riboflavina | 0/6.7% | 82.5%/0 |
| Saccharomyces pastorianus | 11%/2.6% | 2.2%/15.9% |

As can be seen in the experimental results in Table 1, the Candida magnolia-possessing reduction enzyme, the Candida parapsilosis-possessing reduction enzyme, the Rhodococcus erythropolis-possessing reduction enzyme and the Devosia riboflavina-possessing reduction enzyme show a good stereo-specificity.

Example 4: Preparation of ethyl (2RS)-acetoamido-(3S)-hydroxybutanoate

As the enzyme is employed Rhodococcus erythropolis-possessing reduction enzymes with prepared in the above preparation Example and as the substrate is employed ethyl 2-acetoamido-3-oxobutanoate prepared in Example 2.

In a 50 mM phosphoric acid solution (pH 7), the substrate (4 g), glucose (60 mmol), NAD (64 umol) and the reduction enzyme 5 ml (250 mg) are added and reacted at 30° C. Samples are taken at a constant time interval and analyzed with a gas chromatography, and the reaction is terminated when the substrate is completely consumed and is not detected. The resulting reaction solution is extracted 3 times with ethyl acetate, dried under magnesium sulfate, and distilled at a reduced pressure to obtain the title compound of ethyl (2RS)-acetoamido-(3S)-hydroxybutanoate 3.7 g (yield 92%).

Example 5: Preparation of (2RS)-amino-(3S)-hydroxy-butyric acid

In a reactor, ethyl (2RS)-acetoamido-(3S)-hydroxybutanoate 2.0 g and 3N HCl aqueous solution 20 ml are introduced and stirred under reflux at 100° C. for 3 hours. The resulting reaction solution is cooled to a normal temperature, filtered and concentrated at a reduced pressure. Ethanol 15 mL is added into the resulting concentrate, which is stirred under reflux for 30 minutes and then cooled to a normal temperature. The resulted solid is separated with a filtration to obtain the title compound of 2-amino-(3S)-hydroxy-butyric acid 1.26 g (yield 70%) as a white solid.

melting point (mp): 255° C. (dec.)
[α]26/D-28.3° (c=1.1)
$^1$H-NMR (400 MHz, CDCl$_3$): δ 4.24 (m, 1H), 4.14 (d, 0.25H), 3.74 (d, J=4.0 Hz, 1H), 3.48 (d, J=4.8 Hz, 0.25H), 1.23 (d, J=6.8 Hz, 0.75H), 1.11 (d, J=7.6 Hz, 3H).

Comparative Example 5: Preparation of ethyl (2RS)-acetoamido-(3RS)-hydroxybutanoate Ethyl (2RS)-acetoamido-3-oxobutanoate 1.8 g prepared in Example 2 is dissolved in isopropyl alcohol 15 ml and ethanol 15 ml to give a reaction solution, which is cooled to −10° C. To the reaction solution, sodium borohydride (NaBH4) 1.0 g is gradually added with a caution of heat generation. After the completion of addition, the reaction mixture is stirred at a normal temperature for 5 hours, neutralized with 1 N HCl aqueous solution to adjust the pH to 7. The resulting reaction solution is filtered and concentrated. The concentrate is diluted with purified water 20 ml and extracted with ethyl acetate 50 ml 3 times. The organic phases are combined, washed with a saturated aqueous sodium bicarbonate solution 20 ml, and dried with anhydrous magnesium sulfate to obtain the title compound of ethyl (2RS)-acetoamido-(3RS)-hydroxybutanoate 1.36 g (yield 72%).

$^1$H-NMR (400 MHz, CDCl$_3$): δ 6.67 (br s, 1H), 4.65 (q, J=3.2 Hz, 1H), 4.23 (m, 3H), 3.48 (d, J=4.8 Hz, 0.25H), 2.07 (s, 3H), 1.30 (t, J=7.2 Hz, 3H), 1.19 (d, J=6.4 Hz, 3H).

Comparative Example 6: Preparation of (2RS)-amino-(3RS)-hydroxy-butyric acid

In a reactor, ethyl (2RS)-acetoamido-(3RS)-hydroxybutanoate 3.78 g obtained in Comparative Example 5 and 3N HCl aqueous solution 40 ml are introduced and stirred under reflux at 100° C. for 3 hours. The resulting reaction solution is cooled to a normal temperature, filtered and concentrated at a reduced pressure. Ethanol 30 mL is added into the resulting concentrate, which is stirred under reflux for 30 minutes and then cooled to a normal temperature. The resulted solid is separated with a filtration and dried to obtain the title compound of (2RS)-amino-(3RS)-hydroxy-butyric acid 1.83 g (yield 77%) as a white solid.

Melting point (mp): 255° C. (dec.) (The same as in Example 5)
$^1$H-NMR (400 MHz, CDCl$_3$): δ 4.24 (m, 1H), 4.14 (d, 0.25H), 3.74 (d, J=4.0 Hz, 1H), 3.48 (d, J=4.8 Hz, 0.25H), 1.23 (d, J=6.8 Hz, 0.75H), 1.11 (d, J=7.6 Hz, 3H).

Whereas the compound obtained in Example 5 is a mixture of two isomers among all 4 isomers of threonine, the compound obtained in Comparative Example 6 is a mixture containing all 4 isomers of threonine and has been prepared to check whether they have the same chemical structure.

NMR analysis shows that the compound obtained in Example 5 and the compound obtained in Comparative Example 6 have the same structural formula.

INDUSTRIAL APPLICABILITY

The method of the present invention can be applied to the preparation of unnatural isomers of threonine and mixture thereof, which can be employed as a chiral building block in the drug synthesis.

What is claimed is:

1. A method for the preparation of (2RS)-amino-(3S)-hydroxy-butyric acid or its derivative of Formula 5, comprising the steps of:
   (i) reacting 3-oxo-butyric acid alkyl ester of Formula 6 with sodium nitrite to obtain 2-hydroxyimino-3-oxo-butyric acid alkyl ester of Formula 7;
   (ii) reducing or hydrogenating the compound of Formula 7 to obtain (2RS)-alkylcarbonylamino-3-oxo-butyric acid alkyl ester of Formula 8;
   (iii) enzymatically reducing the compound of Formula 8 to obtain (2RS)-alkylcarbonylamino-(3S)-hydroxy-butyric acid alkyl ester of Formula 9; and
   (iv) deprotecting the compound of Formula 9 to prepare (2RS)-amino-(3S)-hydroxy-butyric acid of Formula 5,

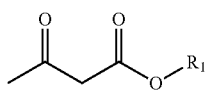
[Formula 6]

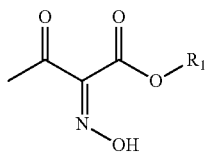
[Formula 7]

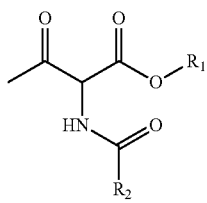
[Formula 8]

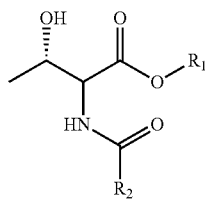
[Formula 9]

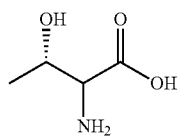
[Formula 5]

wherein, $R_1$ represents hydrogen, a linear or branched $C_1$~$C_4$ alkyl group, an alkylcarbonyl group, an alkoxycarbonyl group, a phenyl group, a benzyl group or a phenethyl group and wherein said alkyl can be unsubstituted or substituted with hydroxy or halogen, wherein $R_2$ represents a linear or branched $C_1$~$C_4$ alkyl group, an alkylcarbonyl group, an alkoxycarbonyl group, a phenyl group, a benzyl group or a phenethyl group, wherein said alkyl can be unsubstituted or substituted with hydroxy or halogen and wherein $R_1$ can be the same or different than $R_2$, and wherein said enzymatic reduction is carried out by employing a reductive enzyme or a fraction containing the reductive enzyme, said reductive enzyme being issued from one or more microbials selected from a group consisting of *Saccharomyces, Lactobacillus, Candida, Rhodococcus, Pseudomonas, Pichia* and *Devosia riboflavina*.

2. The method of claim 1, wherein said hydrogenation of the step (ii) is carried out by using one or more reagent selected from a group consisting of acetic anhydride, di-tert-butyl-dicarbonate and benzyl chloroformate in the presence of palladium/carbon with hydrogen gas.

3. The method of claim 1, wherein said enzymatic reduction is carried out by employing a reductive enzyme or a fraction containing the reductive enzyme, said reductive enzyme being issued from one or more microbials selected from a group consisting of *Candida magnoliae, Candida parapsilosis*, and *Rhodococcus erythropolis*.

* * * * *